United States Patent [19]

Fanning

[11] 4,041,057

[45] Aug. 9, 1977

[54] HYDROESTERIFICATION PROCESS

[75] Inventor: Robert J. Fanning, Farmington Hills, Mich.

[73] Assignee: Ethyl Corporation, Richmond, Va.

[21] Appl. No.: 592,642

[22] Filed: July 2, 1975

[51] Int. Cl.$^2$ .................. C11C 3/02; C07C 67/04; C07C 67/38

[52] U.S. Cl. .................. 260/410.9 R; 260/468 M; 260/488 R; 260/488 K; 260/497 A

[58] Field of Search .................. 260/410.9 R, 488 K, 260/497 A; 423/592, 417; 252/431 N, 416

[56] References Cited

U.S. PATENT DOCUMENTS

| | | | |
|---|---|---|---|
| 2,767,217 | 10/1956 | Moise et al. | 423/417 |
| 2,848,304 | 8/1958 | Yoshida | 423/417 |
| 3,463,741 | 8/1969 | Russell | 252/416 |
| 3,507,891 | 3/1970 | Hearne | 260/410.9 R |
| 3,607,786 | 9/1971 | Nienburg et al. | 252/416 X |
| 3,728,104 | 4/1973 | Coffield | 423/417 X |
| 3,816,337 | 6/1974 | Usami | 260/604 HF |
| 3,856,832 | 12/1974 | Ethyl | 260/410.9 R |
| 3,899,442 | 8/1975 | Friedrich | 260/410.9 R |

Primary Examiner—Winston A. Douglas
Assistant Examiner—John F. Niebling
Attorney, Agent, or Firm—Donald L. Johnson; John F. Sieberth; Shelton B. McAnelly

[57] ABSTRACT

A hydroesterification process is described for preparing esters of carboxylic acids by reacting an olefin, CO and alcohol in the presence of a cobalt catalyst. An important aspect of the present invention is improved catalyst recycle.

7 Claims, 1 Drawing Figure

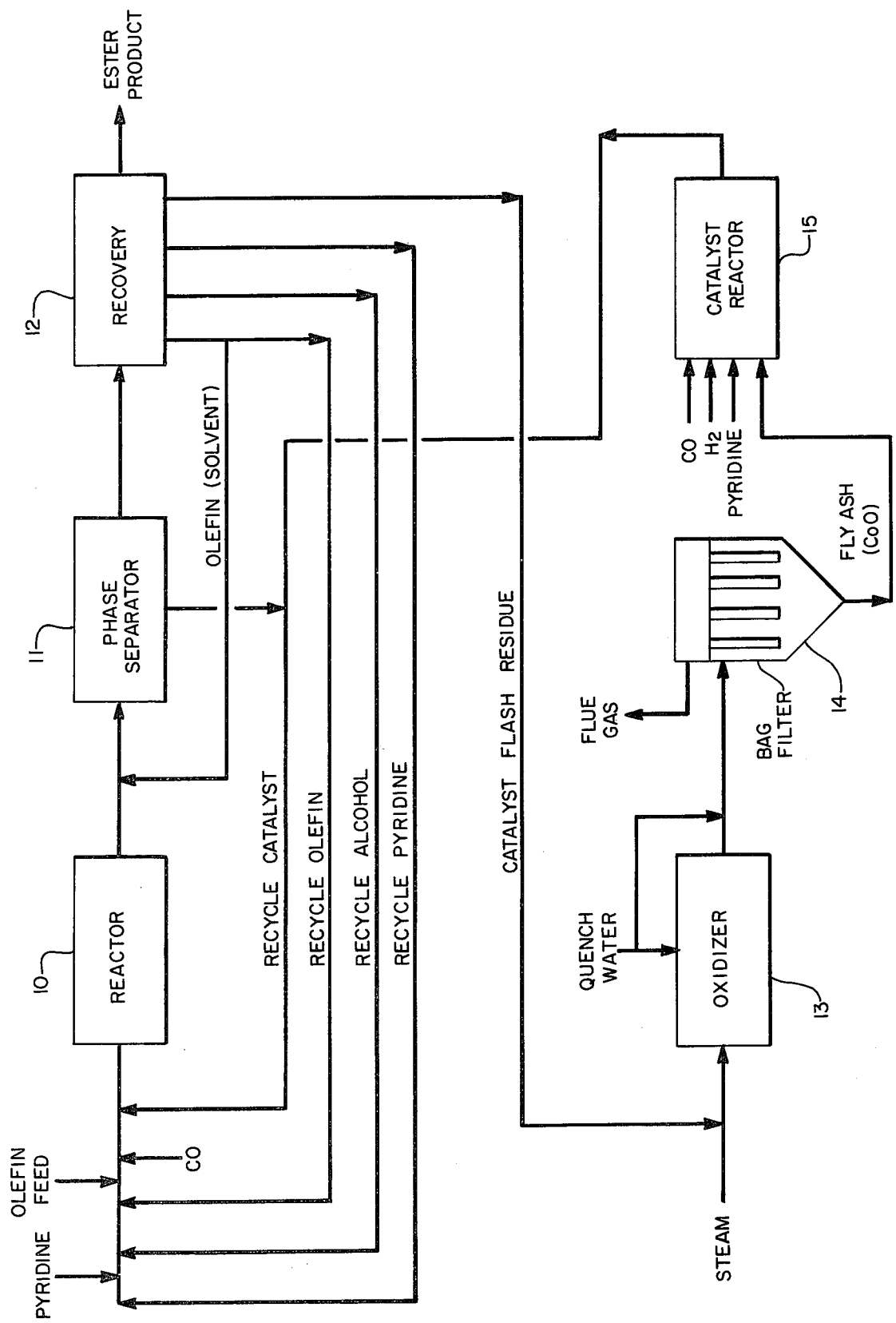

HYDROESTERIFICATION PROCESS

BACKGROUND OF THE INVENTION

The hydroesterification or hydrocarbomethoxylation of olefins and alcohols catalyzed by cobalt catalysts is known, being described for example in U.S. Pat. No. 2,542,767. The use of a small amount of pyridine in combination with hydrogen is known to improve the selectivity of the hydroesterification of propylene. This is described by A. Matsuda and H. Uchida in Chem. Soc. Japan Bull. 38, 710–715 (1965). Relatively large amounts of pyridine alone are also known to promote propylene hydroesterification as disclosed by V. Gankin et al, in Zh. Prikl, Khim. 40, 1862–1864 (1967).

Other discussions of the reaction of olefinic materials with CO in the presence of a cobalt catalyst and a pyridine are contained in U.S. Pat. No. 3,507,891, in U.S.S.R. Pat. No. 173,754 (Sept. 25, 1965), and in Japanese Pat. No. 12,854 (July 21, 1966); in Chem. Abstracts, Vol. 68, 12411$b$ (1968) (page 1169); by Ghankin et al, Zh. Prikl. Khim. (Leningrad 14 (11) 2582-5, Nov. 1968; and by G. Natta, Brennstoff-Chem., 36, 176 (1955).

One of the problems encountered in prior art processing is emphasized by U.S. Pat. 3,507,891 which uses certain substituted pyridines rather than pyridine because of the problem that with pyridinea a direct distillation of product containing the complex formed 10 percent or more metallic cobalt which could not be reconverted readily to catalyst. The present invention avoids this problem and provides a way to recover and recycle the catalyst when using various pyridines, even pyridine itself. As a result, one can obtain high conversion characteristic of the use of pyridine-containing systems without having to use substituted pyridines to overcome the catalyst recycle problem. Athough the present invention is suitable for use with pyridine itself, it also may be applied in conjunction with the substituted pyridines which are useful catalysts such as those set forth in U.S. Pat. No. 3,507,891.

A preferred prior art process for the recovery and recycle of a large part of the cobalt values is disclosed in U.S. Pat. No. 3,856,832 wherein the hydroesterification reaction mixture containing ester product, alkanol and cobalt catalyst obtained on reacting olefin, CO and alkanol is contacted with a normally liquid hydrocarbon in an amount sufficient to dissolve the ester product and then the normally liquid hydrocarbon phase is separated from the alkanol phase. Most of the cobalt catalyst goes to the alkanol phase in active form and is suitably recycled to the hydroesterification reaction. In some instances further improvement in cobalt recovery is desired and it is to this end that the present process is directed.

SUMMARY OF THE INVENTION

In accordance with the present invention, the hydroesterification reaction is suitably performed as in the prior art, preferably using the hydrocarbon extraction process of U.S. Pat. No. 3,856,832 providing a catalyst containing alcohol phase which is recycled to the hydroesterification reaction and a hydrocarbon phase containing the product ester. The hydrocarbon phase additionally contains some alcohol and olefin reactants, a pyridine where such is used and a small amount of cobalt material. The hydrocarbon phase is subjected to evaporation separations, e.g. distillation and flashing whereby the ester product, alcohol, olefin, hydrocarbon and the pyridine where such is used are recovered leaving a tarry residue containing cobalt material. The tarry residue is then burned in an oxygen containing environment whereby the cobalt material is converted to cobalt oxide.

Preferably the cobalt oxide is then reacted with carbon monoxide and hydrogen to produce an active catalyst which is also recycled to the hydroesterification. Because of the beneficial effects attendant thereto, it is usually preferred that the cobalt oxide be converted to the active catalyst in the presence of a pyridine (e.g. 1:1 molar ratio) and that the hydroesterification reaction be conducted in the presence of additional pyridine. An advantage of the present process is that pyridine can be used therein, since the disadvantages discussed in U.S. Pat. No. 3,507,891 connected with the use of pyridine are avoided. Of course, where desired, substituted pyridines such as those of U.S. Pat. No. 3,507,891 are usable in the present process.

Thus the present invention relates to a process for producing esters which comprises reacting olefin having from about 3 to about 40 carbon atoms per molecule with alcohol, preferably alkanol, especially methanol, in the presence of a cobalt carbonyl catalyst system to produce ester in admixture with residual catalyst and residual reactants. From this product mixture there is recovered at least a portion of the ester product producing cobalt-containing catalyst residue which is heated at a temperature of from abut 1000° F to about 4000° F under oxidizing conditions wherein the cobalt of the catalyst residue is converted to cobalt oxide. Preferably, the cobalt oxide thus produced is reacted with carbon monoxide and hydrogen to form active carbonyl catalyst. Preferably, the cobalt carbonyl catalyst is a pyridine complex, especially a 1:1 molar complex of the formula HCo(CO)$_4$.pyridine. In a preferred process in accordance with the present invention, the cobalt carbonyl catalyst formed from the cobalt oxide is recycled to the hydroesterification reaction step to provide at least a portion of the catalyst for the reaction therein.

In a preferred aspect of the present invention, the temperature at the cobalt catalyst residue heating step is from about 1500° F to about 2500° F, especially from about 1900° F to about 2000° F.

In one aspect, the present invention relates to a process for producing esters wherein olefin having from about 3 to about 40 carbon atoms per molecule is reacted with CO and alcohol having from 1 to about 20 carbon atoms per molecule in the presence of cobalt-carbonyl-pyridinium catalyst to produce ester in admixture with residual catalyst. The reaction mass from the preceding step is then combined with olefin of the type reacted in the foregoing and separated into two phases, a first phase consisting essentially of alcohol, a pyridine and cobalt catalyst complex and a second phase consisting essentially of olefin and ester and minor proportions each of catalyst, alcohol and a pyridine. The first phase is recycled to the reacting step and the second phase is purified to recover olefin, product ester, alcohol and a pyridine. producing a residue containing the catalyst.

The residue is then heated at a temperature of from about 1000° F to about 4000° F under oxidizing conditions wherein the cobalt of the catalyst residue is converted to cobalt oxide.

The cobalt oxide is recovered and reacted with CO, hydrogen and a pyridine to form cobalt-carbonyl-pyridinium catalyst. In a complete or cyclic process, the cobalt-carbonylpyridinium catalyst thus formed is recycled to the initial reaction step of the foregoing sequence.

BRIEF DESCRIPTION OF THE DRAWING

With reference now to the FIGURE, a preferred embodiment of the features of the present invention is shown. Olefin, alcohol and CO are reacted at 10 in the presence of cobalt carbonyl catalyst and pyridine promoter. After the reaction, excess CO is flashed from the reaction product, the remainder of the reaction product being combined with hydrocarbon from 12 and then delivered to the phase separator 11.

Two phases are obtained from 11, one phase being mostly active catalyst, alcohol and some pyridine, which is recycled to 10, the other phase being mostly ester product, and olefin with some alcohol, pyridine and catalyst. The latter phase is delivered to recovery 12 where the ester is recovered, the olefin, alcohol and pyridine recovered for recycle to 10 and a catalyst residue produced. The residue is oxidized at 13 providing a cobalt oxide fly ash which is recovered by bag filter 14. Cobalt oxide thus obtained is reacted in catalyst reactor 15 with CO, $H_2$ and pyridine to provide an active catalyst for recycle to reactor 10. Make-up catalyst and pyridine are provided as necessary with feed CO, alcohol and olefins being provided as required.

DESCRIPTION OF THE PREFERRED EMBODIMENTS

In the process of the present invention, olefin, CO and alcohol are reacted at elevated temperature and pressure in the presence of a cobalt carbonyl catalyst system to produce ester,

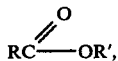

whose acyl groups

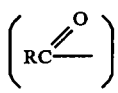

contain one more carbon atom than the starting olefin and whose (—R') group corresponds to the R group of the alcohol (ROH) reacted. Typically, therefore, the reaction of dodecene, CO and methanol produces methyl tridecanoate as product ester.

In a preferred embodiment of the present process, the product from the reaction contains residual olefin and alcohol, ester produced by the reaction, free pyridine, plus the residue of catalyst which includes cobalt carbonyl and pyridine. From this residue, it is desired to remove the residual alcohol and olefin, as much free pyridine as possible, and to recover at least the cobalt value of the catalyst to avoid expense attendant to the use of fresh cobalt catalyst on a one pass basis. A principal problem in the past has been the difficulty of recovering the cobalt value because after the removal of the reactants and ester product, the cobalt, which is still largely in the form of a carbonyl complex, is accompanied by a heavy residue of a tarry or polymeric nature and the separation of the cobalt catalyst from the tarry residue is not readily accomplished. It has been found that the residue can be burned, or oxidized, at an elevated temperature of the order of 1000° to 4000° F which results in the conversion of the residue into ordinary products of combustion; viz, water, $CO_2$, plus a finely-divided fly ash which is mainly cobalt oxide. It has been discovered that recovered cobalt oxide can be reacted with pyridine and carbon monoxide, under conditions similar to those wherein cobalt carbonate is reacted with pyridine, carbon monoxide and hydrogen, to form cobalt-carbonyl-pyridinium catalyst desirably fed for the reaction of olefin, alcohol and CO. Surprisingly, it has been found that the temperature used in the burning of the residue is important with temperatures in excess of 1000° F, especially from 1900° to 2000° F, being preferred.

In the combustion of the residue, it is usually preferred to atomize the residue using steam or compressed air with a gun-type burner similar to those used for burning heavy fuel oil. The burner discharges into a fire box which is cooled by a spray of water or which alternately can be used to supply heat as in the generation of steam, for example. Off-gases from the furnace are preferably cooled to a suitable temperature of the order of 400° F by a water spray so that they can be safely and conveniently passed to a bag-type filter for the recovery of the particulate cobalt oxide contained therein. A typical bag-type filler employs "Nomex" cloth, a synthetic polymer, which temperatures withstand temeratures up to 400° F for prolonged periods. Cobalt oxide thus obtained reacts readily with CO to produce cobalt carbonyl catalyst. The cobalt of the catalyst system can thus be recycled many times.

General aspects of the hydroesterification reaction are set forth in the discussion which follows. The reaction is illustrated by the following reaction equation:

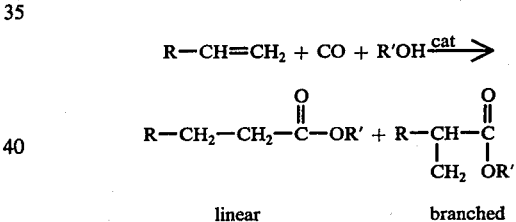

linear      branched

The ester products obtained are mixtures of branched and linear esters. The hydroesterification is ordinarily carried out at elevated temperatures (755° C–200° C) and under pressure ranging from about 500 to about 5,000 p.s.i. Olefins which are used in the hydroesterification process are unsaturated organic compounds having at least one non-aromatic carbon to carbon double bond, and having from 2 to about 40, preferably from 6 to about 24 carbon atoms. They include compounds having other functional groups such as carboxy, carbonyl, halide, aryl groups and the like, provided that these functional groups do not adversely affect the hydroesterification reaction of the present extraction process. Branched as well as straight chain, cyclic and alicyclic olefins are included. Useful olefins are ethyl acrylate, oleic acid, 2-chlorododecene-1,6-phenylundecene-1, ricinoleic acid, 3-hyroxyheptadecene, and the like.

More preferred olefins are hydrocarbon monoolefins including the alpha as well as internal olefins. Examples of useful hydrocarbon monoolefins are ethylene, butene-1, pentene-2, cyclooctene, eicosene-1, hexadecene-2, octacosene-4,4-butyldecene-1, tetracontene-1, 5,7,11-trimethyldodecene-1, and the like. Mixtures of alpha and internal olefins are also useful. In addition, commercial mixtures of olefins obtained for example from Ziegler catalyzed low molecular weight olefins such as ethylene or propylene and those obtained by dehydrogenation of suitable paraffins and the like are also useful. These commercial mixtures are generally mixtures of various homologous olefins such as $C_4$, $C_6$, $C_8$ olefins; $C_{12}$, $C_{13}$, $C_{14}$, $C_{15}$, $C_{16}$ olefins; $C_8$, $C_{10}$, $C_{12}$, $C_{14}$, $C_{16}$ olefins; $C_{30}$–$C_{36}$ olefins; $C_{22}$, $C_{24}$, $C_{26}$ olefins and the like.

Alcohols used are normally liquid alcohols having from 1 to about 20 carbon atoms per molecule, including monohydroxy alcohols, diols, triols, and the like, since esterification is desired. Included are primary, secondary and tertiary alcohols. Monohydroxy alcohols are preferred. Preferred alcohols have an alkyl carbon chain of from 1 to about 5 carbon atoms. Thus, alkanols, e.g., methanol are preferred. Suitable alcohols are 2-dodecanol, tert-butanol, 2-ethylhexanol, cyclohexanol, 2,2-dimethylpropanol, ethanol, n-pentanol, 2-methylpropanol and isopropanol, sec-butanol, and the like.

A cobalt catalyst is used in the hydroesterification process. Any cobalt containing compound capable of forming cobalt carbonyl under the hydroesterification reaction conditions can be used. Thus cobalt nitrate, cobalt salts of $C_2$–$C_{30}$ alkanoic acids, cobalt acetate, cobalt naphthenate, cobalt chloride, cobalt sulfate and the like can be used. Dicobalt octacarbonyl can also be used directly, if preferred.

The concentration of catalyst in the hydroesterification reaction is varied. Generally an amount of catalyst sufficient to provide from 0.005 to 0.10 moles of cobalt per mole of olefin, is used.

Although not required in the hydroesterification reaction, a pyridine promoter can be utilized. Suitable pyridine promoters include pyridine and substituted pyridines such as the halopyridines, alkylpyridines, quinolines, cyanopyridines, acylpyridines, nitropyridines, and the like. Preferred pyridines are those which have no substituent in the alpha position. They are exemplified by $C_1$–$C_6$ alkylpyridines ($\beta$-picoline, 4-ethyl-3,5-dimethylpyridine, 4,4-trimethylenedipyridine, 3-hexylpyridine, 3,5-dimethylpyridine, 3,5-diethylpyridine, 4-cyclohexylpyridine); acylpyridines (3-butyrylpyridine, 4-propionylpyridine, 4-acetyl-3-methylpyridine), and the like. Other useful pyridine promoters are described in U.S. Pat. No. 3,507,891, issued Apr. 21, 1970. Pyridine is a most preferred promoter.

When used, the amount of pyridine promoter can be varied over a wide range. A practical upper limit is about 250 moles of pyridine promoter per mole of cobalt in the catalyst, although greater amounts can be used. A preferred range is 6–50 moles of pyridine promoter per mole of cobalt.

The pyridine promoter effects improvement in the reaction rate and/or the ratio of linear to branched ester product obtained in the hydroesterification reaction. An improved hydroesterification process featuring the use of a pyridine promoter is disclosed in U.S. Application Ser. No 883,308, filed Dec. 8, 1969, now abandoned, and is incorporated hereby by reference.

The hydroesterification reaction mixture usually contains some unreacted alkanol, some olefin, cobalt catalyst and any promoter, if a promoter was used. The reaction mixture is cooled to about room temperature or below and then it is treated with a quantity of a normally liquid hydrocarbon, preferably the same olefin as used in the hydroesterification reaction.

In general, hydrocarbons which are suitable for this treatment should be fairly good solvents for the ester products of the hydroesterification and fairly poor solvents for the alkanol reactant of the hydroesterification. Useful hydrocarbons include $C_5$–$C_{20}$ alkanes (e.g., 2-methylpentane, pentane, cyclohexane, eicosane, tetradecane, and the like), $C_6$–$C_{30}$ olefins (e.g., hexene, triacontene, heneicosene and the like), and mixtures thereof. In some instances, alkanes having 5 to about 10 carbon atoms are preferred. Examples of preferred alkanes are heptane, isooctane, pentane, decane, nonane, mixtures of these alkanes, and the like.

The reaction mixture is treated with an amount of hydrocarbon sufficient to extract the ester product out of the reaction mixture. The optimum amount of hydrocarbon to be used will depend on the solubility characteristics of the hydrocarbon, the ester product and the alkanol. Up to about 10 volumes of hydrocarbon per volume of reaction mixture can be used. Ordinarily, from about one-quarter to about six volumes of hydrocarbon per volume of reaction mixture is conveniently used; and 0.5 to 4 volumes of hydrocarbon per volume of reaction mixture is preferred; about 1 to 4 volumes of hydrocarbon per volume of reaction mixture is more preferred.

The reaction mixture is treated with the hyrocarbon in such a way as to ensure intimate contact between the two liquids in order to effect extraction of the ester product. After this treatment with the hydrocarbon, a two-phase system is obtained. The upper phase contains principally the hydrocarbon solvent, the ester product and substantially all of the unreacted olefin, while the lower phase contains principally alkanol and substantially all of the cobalt catalyst. Both phases also contain some promoter if one was used. The ester containing hydrocarbon layer is then separated from the cobalt containing alkanol layer. The ester is recovered from the hydrocarbon solvent using conventional means; and the hydrocarbon solvent can be reused for additional cobalt catalyst extractions. The alkanol layer contains substantially all of the cobalt catalyst from the hydroesterification mixture; and the catalyst is in an active form which can be used directly to catalyst another hydroesterification reaction. By substantially all, I mean at least about 70 percent of the total cobalt containing catalyst charged in the hydroesterification reaction. Active catalyst recoveries of 80 percent or more and 90 percent or more of the total cobalt catalyst charged are preferred. If desired, this alkanol solution of recovered catalyst can be reused in volume by distilling alkanol from the solution. However, the catalyst solution is more conveniently recycled directly into a hydroesterification reaction mixture where the alkanol becomes a reactant. Since the cobalt catalyst is sensitive to air, usual precautions are taken to prevent unnecessary exposure of the catalyst solution to air both during and subsequent to the recovery process.

In order to facilitate the catalyst recovery, it is preferred that the reaction mixture contain a certain amount of alkanol. The amount of alkanol should be sufficient to dissolve the active cobalt catalyst species and result in a two-phase system after treatment with the hydrocarbon which extracts the ester product. To ensure that a sufficient excess of alkanol is present in the reaction mixture, it is preferred that the hydroesterification process be carried out using a stoichiometric excess based on the olefin reactant or alkanol reactant. For example olefin:alkanol molar reactant ratios of 1:1.1 to 1:6 or higher can be used; with 1:1.5 to 1:3 olefin:alkanol ratios being preferred. If a stoichiometric amount of alkanol, i.e., a molar ratio of olefin:alkanol of 1:1, is used, a sufficient amount of unreacted alkanol can be ensured if the conversion of olefin is kept below 100 percent. By conversion is meant the percent of olefin which has reacted to form ester. In the event that insufficient unreacted alkanol remains after the hydroesterification has taken place, then an amount of alkanol, sufficient to dissolve the cobalt catalyst and effect a two-phase system after treatment with hydrocarbon, is added to the reaction mixture prior to or simultaneously with the hydrocarbon; and although any alkanol can be used, it is preferred that the alkanol added be the same as the one used in the hydroesterification reaction.

The following example indicates a preferred embodiment and aspect of the present invention.

EXAMPLE

A hydroesterification reactor 10 is used which is of a long tubular configuration. To this reactor is fed on an hourly basis, 171 pounds of $C_{12}$ olefin, 4.62 pounds of cobalt in the form of a cobalt-carbonyl-pyridinium complex ($HCo(CO)_4$·pyridine), 65.3 pounds of methanol, 49.2 pounds of pyridine and 24.4 pounds of carbon monoxide. Reactor temperature is 296°–304° F, and the pressure is 1925 psig. Residence time is 1.5 hours.

The effluent is cooled to about 95° F and pressure is dropped to 200 psig where most of the excess CO flashes off. Additional CO is flashed off in a second stage flash.

Afer removal of the CO, the product of the hydroformulation reactor 10 is mixed with an equal volume of $C_{12}$ olefin recycled from 12 and the mixture is allowed to separate in phase separator 11. A bottoms stream is withdrawn from phase separator 11 and recycled to the hydroformulation reactor 10. This stream is mainly a methanol solution of the pyridine and cobalt catalyst complex. It contains 6–15 weight percent cobalt and provides a very active catalyst which can be recycled indefinitely (40 times or more) without difficulty since impurities go out of the top of phase separator 11. This bottom stream contains about 90–97 percent of the cobalt catalyst in the effluent from reactor 10.

The rest of the cobalt catalyst in the effluent from reactor 10 goes to the top layer effluent from phase separator 11. This effluent contains mostly the olefin recycled from recovery 12 (52 wt. percent), the product esters of the effluent from reactor 10 (31 percent), methanol 8 percent, pyridine 9 percent and from 200 to 1000 ppm of cobalt. This cobalt is from 3 to 10 percent of the catalyst from reactor 10 and must be recovered economically to provide a low cost process.

Recovery 10 is a plural step distillation-flash operation wherein the product ester is recovered, the methanol and pyridine are recovered for recycle to reactor 10 and the olefin is recovered for recycle to mix with the effluent from 10 and as feed for reactor 10. This leaves a tarry residue containing from about 3 to about 8 percent of cobalt by weight. This residue is not active catalyst for the hydroesterification reaction and it will not react with carbon monoxide and hydrogen. This residue is a black, viscous liquid which is easily pumpable at 200° F.

On a typical proportions basis, for each 100 pounds fed from phase separator 11 to recovery 12 a first step distillation in recovery 12 provides as an overhead therefrom 17 pounds of recycle methanol and pyridine which for convenience are in a single line recycle to 10. The 83 pounds of bottoms from the first step distillation in 12 is then split in a flash distillation column to provide 81 pounds of olefin and ester and two pounds of catalyst flash residue.

The catalyst residue from 12 is atomized and burned in excess oxygen environment in furnace oxidizer 13 to provide a material that will subsequently react with CO and $H_2$ to provide an active catalyst for the hydroesterification reaction. Combustion temperatures of from about 1000° F to about 4000° F are typical, from about 1500° F, especially from 1900° F–2000° F, being preferred. As a result of the combustion, the oxidizer effluent contains $CO_2$, $H_2O$, $N_2$ and $O_2$ plus a fly-ash species of cobalt oxide. After cooling, this effluent is filtered in bag filter 14 to retain the cobalt oxide. Typically, the stream is delivered to the bag filter at about 400° F or otherwise as necessary to avoid exceeding the maximum temperature permissible for the filter 14. Cooling is readily effected by spraying water into the effluent stream from 13.

The cobalt oxide recovered at 14 is directly usable in a reaction with CO, $H_2$ and pyridine to produce fresh catalyst which can be recycled to reactor 10.

The following is a typical procedure for catalyst reactor 15 whereby the recovered cobalt oxide is converted to an active catalyst.

To a one-liter stainless steel autoclave was catalyst heel. Then 100 grams of cobalt oxide fly ash (45.1 wt. percent Co) and 200 grams of pyridine were combined to form a slurry and added to the autoclave. The autoclave was closed, flushed with nitrogen to remove the oxygen, then flushed with carbon monoxide to remove the nitrogen. A stepwise pressurization procedure was then followed.

1 — Pressure to 650 psig with $H_2$.
2 — Pressure to 1300 psig with CO.
3 — Heat to 140° C (pressure rises to about 1600 psig then begins to drop).
4 — Then pressure to 2000 psig with CO.
5 — When pressure drops to 1900 psig, pressure to 2000 psig with $H_2$.
6 — When pressure drops to 1900, pressure to 2000 with CO.
7 — Repeat 5 and 6 for a total of 6 pressurizations to 2000 with $H_2$ and a total of 6 pressurizations to 2000 with CO.
8 — Thereafter pressurize from 1900 to 2000 with CO only for 14 additional pressurizations.

At this stage, the temperature is allowed to drop to room temperature, the pressure released, the autoclave contents stirred vigorously and filtered. The liquid product was analyzed, indicating 9.7 percent cobalt and 0.6 percent iron. From material balance data, 98 percent conversion of the cobalt oxide fly ash occurred. The catalyst was found to be active in the reaction at 10.

I claim:
1. A process for producing esters which comprises:
    A. reacting olefin having from about 3 to about 40 carbon atoms per molecule, CO and alcohol having from about 1 to about 20 carbon atoms per molecule in the presence of cobalt carbonyl catalyst to produce ester in admixture with residual catalyst and residual reactants,
    B. recovering at least a portion of the ester product from said reaction thereby producing a cobalt-containing catalyst residue,

C. heating the catalyst residue at a temperature of from about 1000° F to about 4000° F under oxidizing conditions wherein the cobalt of the catalyst residue is converted to cobalt oxide, D. reacting the cobalt oxide with carbon monoxide and hydrogen to form a cobalt carbonyl complex, and E. recycling the cobalt carbonyl complex to the olefin-CO-alcohol reaction step to provide at least a portion of the catalyst therein.

2. A process in accordance with claim 1 wherein the alcohol is an alkanol.

3. A process in accordance with claim 1 wherein the alcohol is methanol.

4. A process in accordance with claim 1 wherein the cobalt carbonyl catalyst is of the formula $HCo(CO)_4$.pyridine.

5. A process in accordance with claim 1 wherein the temperature at the heating step is from about 1500° F to about 2500° F.

6. A process in accordance with claim 1 wherein the temperature at the heating step is from about 1900° F to about 2000° F.

7. A process for producing esters which comprises:

A. reacting olefin having from about 3 to about 40 carbon atoms per molecule, CO and alcohol having from 1 to about 20 carbon atoms per molecule in the presence of cobalt carbonyl-pyridinium catalyst to produce ester in admixture with residual catalyst.

B. combining the reaction mass from the preceding step with olefin of the type reacted at A and separating the resulting mixture into two phases, a first phase consisting essentially of alcohol, a pyridine and cobalt catalyst complex and a second phase consisting essentially of olefin and ester and minor proportions each of catalyst, alcohol and a pyridine, C. recycling the first phase to the reacting step, D. purifying the second phase to recover olefin, product ester, alcohol and a pyridine, producing a residue containing the catalyst, E. heating the residue at a temperature of from about 1000° F to about 4000° F under oxidizing conditions wherein the cobalt of the catalyst residue is converted to cobalt oxide, F. recovering the cobalt oxide, G. reacting the recovered cobalt oxide with CO, hydrogen and a pyridine to form cobalt carbonyl-pyridinium catalyst, H. and recycling the cobalt carbonyl-pyridinium catalyst formed in step G to the reaction at step A.

* * * * *

UNITED STATES PATENT OFFICE
CERTIFICATE OF CORRECTION

PATENT NO. : 4,041,057
DATED : August 9, 1977
INVENTOR(S) : Robert J. Fanning

It is certified that error appears in the above-identified patent and that said Letters Patent are hereby corrected as shown below:

Column 1, line 15, "Prikl," should read -- Prikl. --. Column 1, line 22, "(Leningrad 14" should read -- (Leningrad) 14 --. Column 1, line 28, "pyridinea" should read -- pyridine --. Column 2, line 34, "active carbonyl" should read -- active cobalt carbonyl --. Column 2, line 61, "pyridine." should read -- pyridine, --. Column 3, line 1, "cobalt-carbonylpyridinium" should read -- cobalt-carbonyl-pyridinium --. Column 3, line 12, "combinedwith" should read -- combined with -- Column 4, lines 26-27, "which temperatures withstand temperatures" should read -- which will withstand temperatures -- Column 4, line 46, "(755°C-200°C)" should read -- (75°C-200°C)--. Column 5, line 42, "4,4-trimethylenedipyridine," should read -- 4,4'-trimethylenedipyridine, --. Column 7, line 9, "terification has taken place" should read -- terification reaction has taken place --. Column 8, line 12, "1500°F, especially from" should read -- 1500°F to about 2500°F, especially from --. Column 8, line 28, "steel autoclave was catalyst heel." should read -- steel autoclave was added 10 grams of a previously made catalyst "heel". --.

Signed and Sealed this

Fifth Day of June 1979

[SEAL]

Attest:

RUTH C. MASON
Attesting Officer

DONALD W. BANNER
Commissioner of Patents and Trademarks